United States Patent [19]

Haynes

[11] Patent Number: 5,310,403
[45] Date of Patent: May 10, 1994

[54] IONTOPHORETIC DRUG DELIVERY DEVICE AND CIRCUIT THEREFOR

[75] Inventor: John L. Haynes, Chapel Hill, N.C.

[73] Assignee: Becton, Dickinson and Company, Franklin Lakes, N.J.

[21] Appl. No.: 884,684

[22] Filed: May 18, 1992

[51] Int. Cl.⁵ .............................................. A61N 1/30
[52] U.S. Cl. ........................................ 604/20; 607/154
[58] Field of Search ................... 604/20; 128/798, 802, 128/803

[56] References Cited

U.S. PATENT DOCUMENTS

| | | | |
|---|---|---|---|
| 2,047,308 | 7/1936 | Chapman. | |
| 3,991,755 | 11/1976 | Vernon et al. | 604/20 |
| 4,141,359 | 2/1979 | Jacobsen et al. | 604/20 |
| 4,211,222 | 7/1990 | Tapper | 604/20 |
| 4,325,367 | 4/1982 | Tapper | 604/20 |
| 4,416,274 | 11/1983 | Jacobsen et al. | 604/20 |
| 4,708,716 | 11/1987 | Sibalis | 604/20 |
| 4,725,263 | 2/1988 | McNichols et al. | 604/20 |
| 4,731,926 | 3/1988 | Sibalis | 604/20 |
| 4,820,263 | 4/1989 | Spevak et al. | 604/20 |
| 4,950,229 | 8/1990 | Sage, Jr. | 128/798 |
| 5,087,240 | 2/1992 | Sibalis | 604/20 |
| 5,135,478 | 8/1992 | Sibalis | 604/20 |

FOREIGN PATENT DOCUMENTS

| | | | |
|---|---|---|---|
| 91/06534 | 4/1992 | PCT Int'l Appl. | 604/20 |
| 9115257 | 10/1991 | World Int. Prop. O. | 604/20 |

Primary Examiner—C. Fred Rosenbaum
Assistant Examiner—Michael Rafa
Attorney, Agent, or Firm—Allen W. Wark

[57] ABSTRACT

An iontophoresis system includes an iontophoretic drug delivery device for placement against the skin of a patient and having at least one segmented electrode, and a circuit for controlling and equalizing current passing through each of a plurality of electrode segments. The current controlling circuit includes a plurality of constant current sources, each of which is electrically coupled to a corresponding one of the electrode segments. The constant current sources are selected such that substantially the same amount of current flows through each electrode segment independent of the impedance of the skin of the of the patient.

7 Claims, 7 Drawing Sheets

IONTOPHORETIC DRUG DELIVERY DEVICE AND CIRCUIT THEREFOR

BACKGROUND OF THE INVENTION

1. Field of the Invention

The present invention relates to iontophoretic devices for delivering a drug or medicant to a patient transdermally, i.e., through the patient's skin, and more specifically relates to an iontophoretic device having one or more segmented electrodes and current delivery circuits therefor.

2. Description of the Prior Art

Conventional iontophoretic devices, such as described in U.S. Pat. No. 4,820,263 which issued to Richard Spevak et al., for delivering a drug or medicant transdermally, basically consists of two electrodes—an anode and a cathode. Electric current is driven from an external supply into the patient's skin at the anode, and back out at the cathode. Most modern iontophoretic devices are powered by a constant current source to ensure that the current is kept at a desired level despite differences in skin impedance among individuals.

Electrode structures for iontophoretic devices generally have an active electrode (for example, the anode) which delivers the ionic medication, and an indifferent electrode (for example, the cathode) with an electrolyte. The active and indifferent electrodes are connected to the skin forming a circuit. The current passes from a power source through one of the electrodes to the skin, through the skin and into the subdermal tissue, back out through the skin at a separate location and then through the other electrode. Regulation of the rate of drug delivery has been controlled by the amount of current flow.

It has been found in such iontophoretic devices that skin irritation is related to the current density of the applied current. Densities below 200 $\mu a/cm^2$ are considered as generally being non-irritating. Current densities above that figure are often associated with skin irritation.

A typical iontophoresis system may include electrodes (an anode and a cathode) which are each 5 square centimeters in size through which a total current of 1 milliamperes is driven. At such values, an average current density of 200 $\mu a/cm^2$ is applied to the skin.

If the skin varies considerably in resistance over the area of the electrodes, the peak current densities in different areas of the skin under the electrodes may be considerably higher than the average current density. It has been found that these variations in current density may be as much as 5 or 10 to 1, that is, a more conductive skin area can run at a current density of as much as 10 times the average current density, causing skin irritation or burns in that more conductive area of the skin.

Various electrode arrangements have been suggested to avoid burns and irritation where the iontophoresis or transdermal drug delivery takes place. For example, U.S. Pat. No. 4,211,222 which issued to Robert Tapper, discloses an iontophoretic electrode array for use in transdermal transport of ionic medicants which includes a plurality of positive and negative electrodes for establishing electric field lines in an area and for transmission of ions along the lines. Also, U.S. Pat. No. 4,416,274 which issued to Stephen C. Jacobsen et al. discloses an iontophoretic bioelectrode which includes a receptacle for holding an ionic medication formed with a plurality of separate cube-shaped compartments to help control the distribution of the medication or drug over the area of the bioelectrode. However, such conventional electrode arrays do not prevent excessive current from being drawn through the patient's skin from portions of the electrode contacting areas of the skin which have a significantly lower skin impedance than at other areas.

OBJECTS AND SUMMARY OF THE INVENTION

It is an object of the present invention to provide an iontophoretic device having a pair of electrodes in which the current density of the applied current remains substantially constant over the entire area of the electrodes.

It is another object of the present invention to provide an iontophoresis system for delivery of drug transdermally to a patient, which system includes a drug delivery device attachable to a patient and having at least one segmented electrode and a current delivery circuit for the device.

It is a further object of the present invention to provide an array of electrodes and circuit for an iontophoretic device which minimizes the variation in current density over the surface of the electrodes.

It is yet another object of the present invention to provide a circuit for use with an iontophoretic drug delivery device having a segmented electrode, which circuit controls the amount of current flowing through each electrode segment.

It is still a further object of the present invention to define an iontophoretic device which overcomes the inherent disadvantages of known devices.

In accordance with one form of the present invention, an iontophoresis system includes an iontophoretic drug delivery device for placement against the skin of a patient, the device including at least one segmented electrode, and a circuit for controlling and preferably equalizing current passing through each of the segments of the electrode.

More specifically, the iontophoretic drug delivery device of the system includes a first electrode, which may act as a cathode, and a container or other structure for holding an electrolyte situated in relation to the first electrode such that the electrolyte is in electrical communication with the first electrode. The drug delivery device also includes a second electrode, which may act as an anode, and a container or other structure for holding an ionic medication situated in relation to the second electrode such that the medication is in electrical communication with the second electrode. At least one of the anode or cathode (i.e., the second or first electrode) is formed of a plurality of electrode segments which are spaced apart from one another.

The circuit for controlling current passing through each of the electrode segments includes a plurality of constant current sources. Each of the constant current sources is electrically coupled to a corresponding one of the electrode segments. The constant current sources are selected such that substantially the same amount of current or a desired amount of current flows through each electrode segment, preferably independent of the impedance of the skin of the patient.

In an alternative form of the present invention, the circuit for controlling current passing through each of the electrode segments includes at least one constant current source coupled to each of the electrode segments through one or more commutating or multiplexer circuits. The commutating circuit time multiplexes the delivery of current from the constant current source sequentially to each of the electrode segments so that each segment receives a desired amount of current for a selected amount of time.

These and other objects, features and advantages of the present invention will become apparent from the following detailed description of illustrative embodiments thereof, which is to be read in connection with the accompanying drawings.

DETAILED DESCRIPTION OF THE PREFERRED EMBODIMENTS

Figure 1:
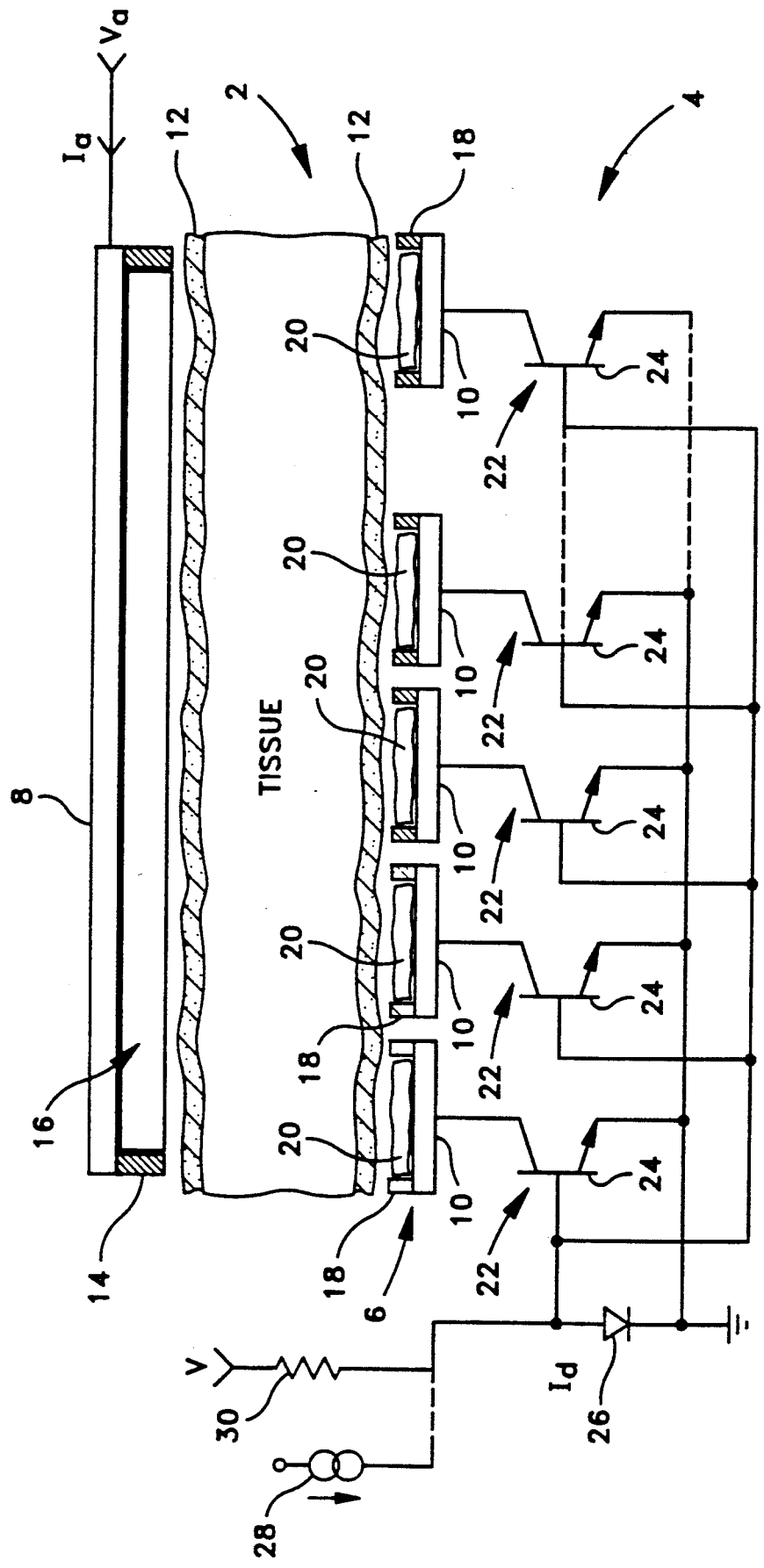
FIG. 1 is a cross-sectional view of an iontophoretic drug delivery device and a current delivery circuit for the same, formed in accordance with the present invention.

Referring initially to FIG. 1 of the drawings, it will be seen that an iontophoresis system for delivering ionic medication to a patient transdermally, that is, through the skin of the patient, basically includes an iontophoretic drug delivery device 2 for placement against the skin of the patient, which device includes at least one electrode formed from a plurality of segments, and a circuit 4 for controlling the current flowing through each of the electrode segments.

More specifically, the iontophoretic drug delivery device 2 of the system includes a first electrode 6, which may act as a cathode, and a second electrode 8, which may act as an anode. At least one of the first and second electrodes 6,8 is formed from a plurality of electrode segments 10 which are spaced apart and separate from each other. In the embodiment shown in FIG. 1, it is the cathode or first electrode 6 which is split into a plurality of electrode segments 10. The iontophoretic drug delivery device is placeable against the skin 12 of a patient so that the anode electrode 8 and cathode electrode 6 are in electrical communication with the patient's skin.

Adjacent to the anode (i.e., second electrode 8) is a container or other suitable structure 14 defining a well for holding an ionic medication 16 in place between the anode and the skin of the patient. Similarly, adjacent to the cathode (i.e., the first electrode 6) is a container or other suitable structure 18 forming a well for holding an electrolyte 20 in place between the cathode and the skin of the patient. If the cathode is split into electrode segments 10, as shown in FIG. 1, then each segment may have adjacent to it a container 14 defining a well for holding the electrolyte 20.

When a voltage $V_a$ is impressed across the first and second electrodes 6,8, current $I_a$ will flow through the skin of the patient, driving the ionic medication into the skin and tissue to be absorbed by the patient's body.

The iontophoresis system of the present invention also includes a current delivery circuit 4 which controls and, in one form of the invention, equalizes the current passing through each of the electrode segments 10. The current controlling circuit includes a plurality of constant current sources 22, where each of the constant sources 22 is electrically coupled to a corresponding one of the electrode segments 10 of whichever electrode is split. The constant current sources 22 are selected such that substantially the same amount of current or a desired amount of current flows through each electrode segment, preferably independent of the impedance of the skin of the patient.

In one form of the present invention, and as shown in FIG. 1 of the drawings, each constant current source 22 may be formed as a current mirror circuit. More specifically, each current mirror circuit includes a transistor 24 which is electrically coupled to a corresponding electrode segment 10. As shown in FIG. 1, the transistors 24 are NPN types having their collectors connected to a corresponding electrode segment of the cathode (i.e., the first electrode 6) of the iontophoretic device. The emitters of each transistor 24 are connected together to ground or other lower potential, as well as being connected to the cathode of a reference diode 26. The bases of each transistor are connected together and to the anode of the reference diode 26.

The current mirror circuits and reference diode are driven by either a constant current source 28 or a voltage source V through a resistor 30 to provide a constant current $I_d$ through the reference diode 26, and will bias the diode and transistors to the on state. As is well known from current mirror circuits, the current through each transistor 24 will be forced to be substantially equal to the current through the reference diode 26, as long as the transistors are not saturated. Accordingly, the current flowing through each electrode segment 10 of the cathode can be controlled and will be equal to that flowing through any other transistor and electrode segment. The current flowing through the electrode segments and each transistor will also be substantially independent of the impedance of the skin of the patient situated adjacent to the electrode segment, as the current, $I_a$, flowing into the anode of the device and through the patient's tissue will be equally divided among all of the transistors 24, irrespective of the impedance of the skin situated adjacent to any cathode segment 10.

Figure 2:
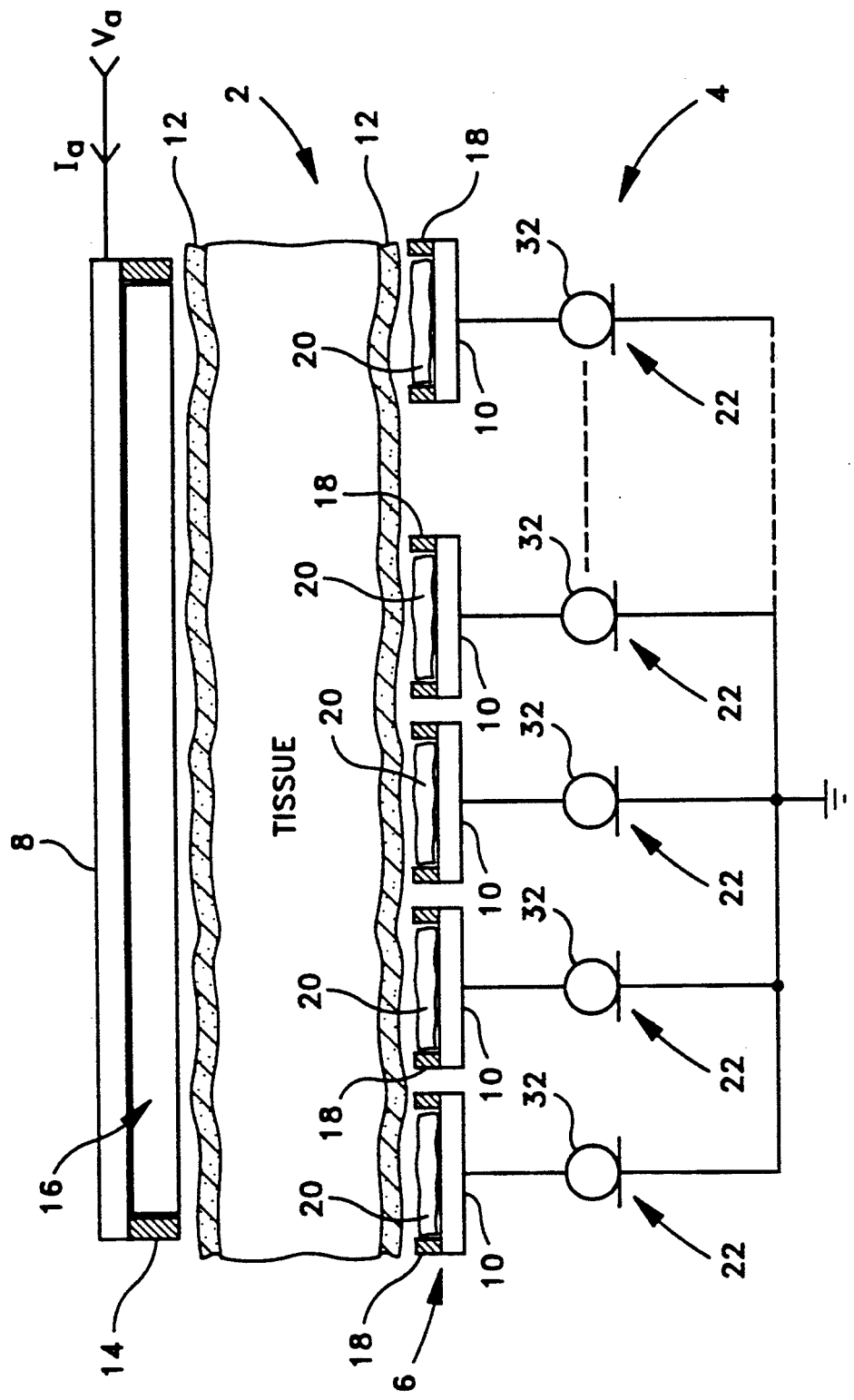
FIG. 2 is a cross-sectional view of an alternative embodiment of a drug delivery device and a current delivery circuit for the device formed in accordance with the present invention.

An alternative embodiment of the present invention is shown in FIG. 2. Instead of using current mirror circuits, as shown in FIG. 1, a plurality of current diodes 32 may be used as the constant current sources. Each current diode 32 is connected to a corresponding one of the electrode segments 10, and the current diodes are selected such that substantially the same amount of current flows through each electrode segment, or predetermined different amounts of current flow through the electrode segments, preferably independent of the impedance of the skin of the patient situated adjacent to each electrode segment.

It is envisioned, of course, to either form the current mirror circuits shown in FIG. 1 or the current diodes 32 shown in FIG. 2 with discrete components or to form such circuits and diodes on a single substrate in an integrated circuit. It is also envisioned that either the cathode or the anode electrode, or both, may be split into a plurality of electrode segments.

Figure 3:
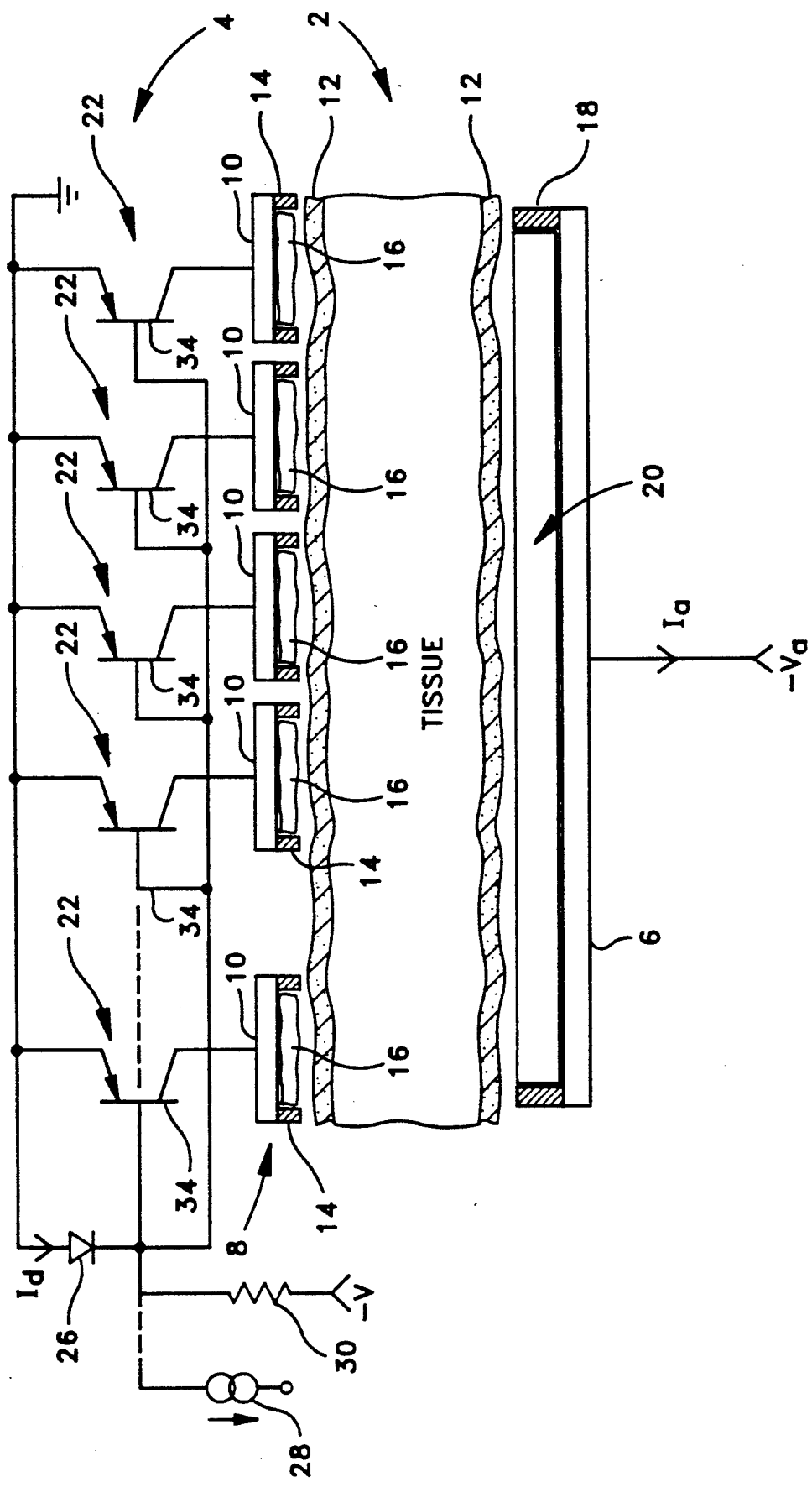
FIG. 3 is a cross-sectional view of a third alternative embodiment of an iontophoretic drug delivery device and a circuit therefor, formed in accordance with the present invention.
Figure 4:
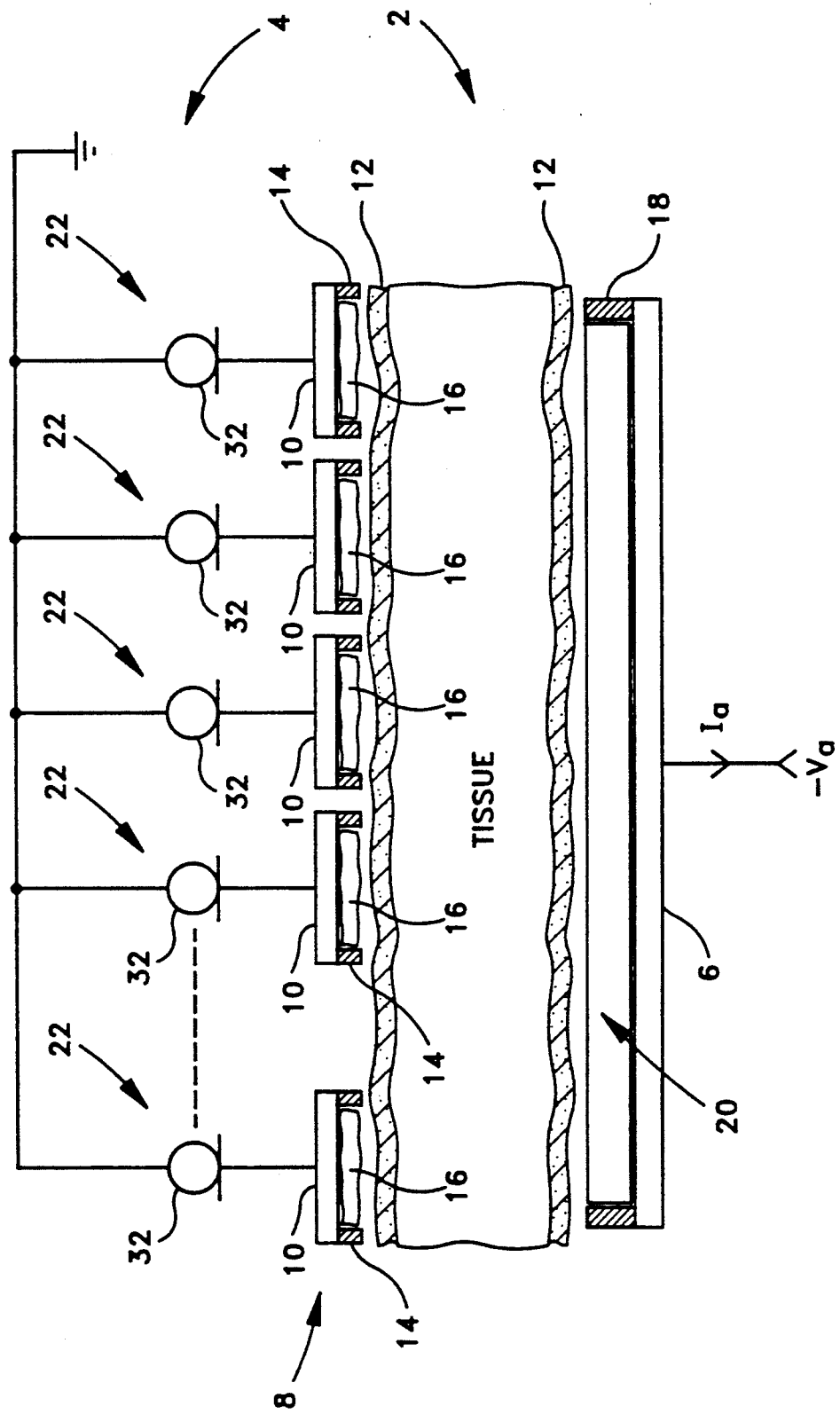
FIG. 4 is a cross-sectional view of a fourth alternative embodiment of a drug delivery device and circuit therefor, formed in accordance with the present invention.

FIGS. 3 and 4 show embodiments of the present invention where the anode (i.e., the second electrode 8) is formed from a plurality of electrode segments 10. The current flowing through each of the electrode segments of the anode is controlled by a constant current source 22. As shown in FIG. 3, the constant current source 22 is a current mirror circuit connected to a reference diode 26, and having a similar configuration as the current mirror circuits shown in FIG. 1. The transistors 34 may be of a PNP type with their emitters connected to ground or a higher potential than the cathode electrode 6, and with their collectors connected to anode electrode segments 10. The bases of transistors 34 are connected to the cathode of reference diode 26, whose anode is connected to the same potential (or ground) as the emitters of transistors 34. The cathode of diode 26 is connected to a current source 28 or lower voltage potential $-V$ through a resistor 30 to bias the reference diode and the transistors to the on state.

Similarly, and as shown in FIG. 4, the current flowing through each segment of the anode electrode may be controlled by using current diodes 32 connected to corresponding electrode segments 10, in the same manner as that shown in FIG. 2.

Figure 5:
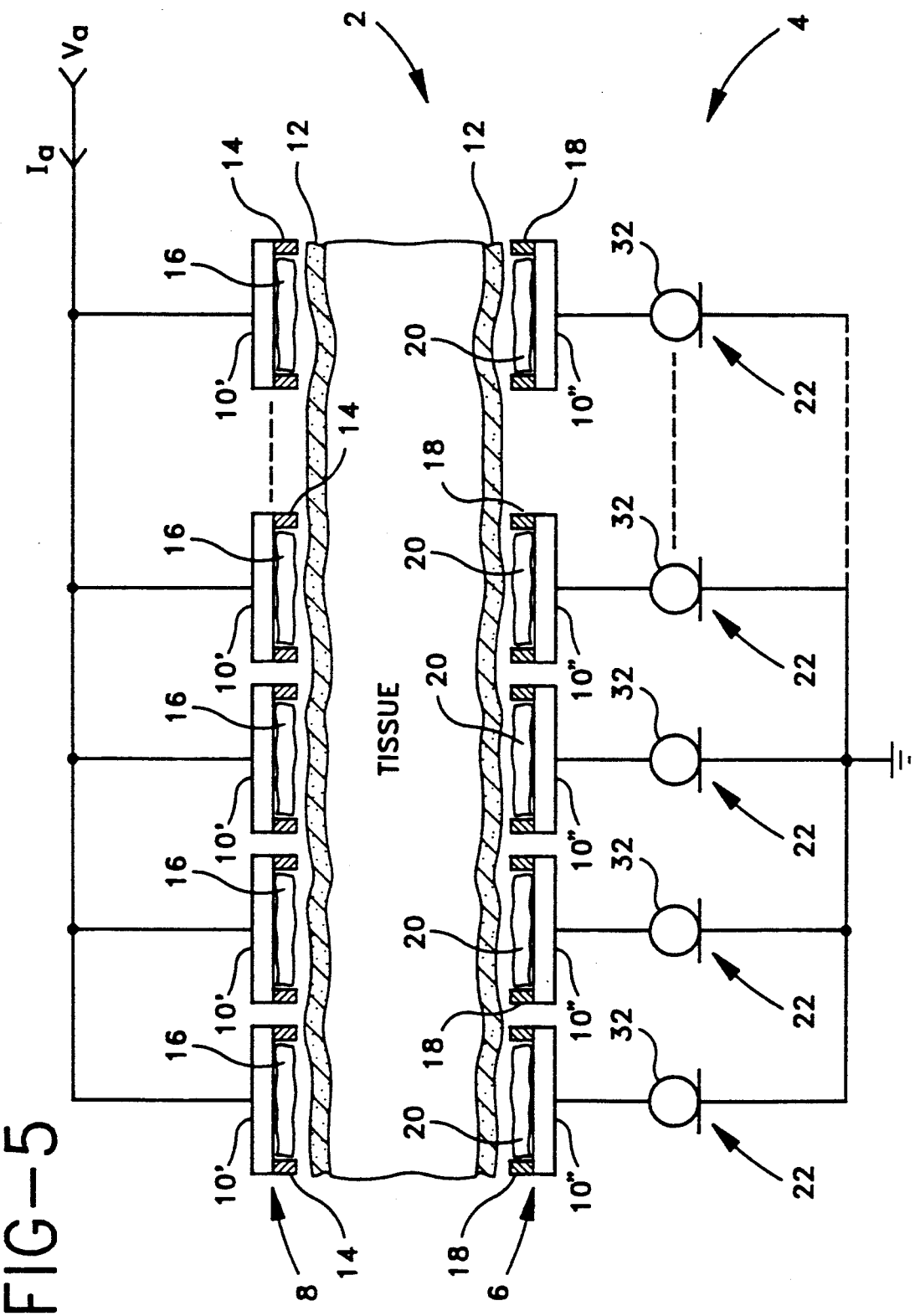
FIG. 5 is a cross-sectional view of a fifth embodiment of a drug delivery device and circuit therefor, formed in accordance with the present invention.

As mentioned previously, and as shown in FIG. 5, both the anode electrode 8 and the cathode electrode 6 may be split into a plurality of electrode segments, 10' and 10'', respectively. In the embodiment shown in FIG. 5, voltage $V_a$ is impressed across and provided to anode electrode segments 10' and cathode electrode segments 10'' such that a total current $I_a$ will flow through the anode and cathode electrodes 8, 6. Each cathode electrode segment 10'', as shown in FIG. 5, is coupled to a constant current source 22, such as current diodes 32 or current mirror circuits, in the same manner as shown in FIGS. 1 and 2. Additionally, each anode electrode 10' is coupled to a constant current source, such as a current diode 32 or current mirror circuit in the same manner as shown in FIGS. 3 and 4. A constant and desired amount of current will flow through each of the anode and cathode electrode segments 10', 10'', irrespective of the impedance of the patient's skin in contact with any of the electrode segments.

Figure 6:
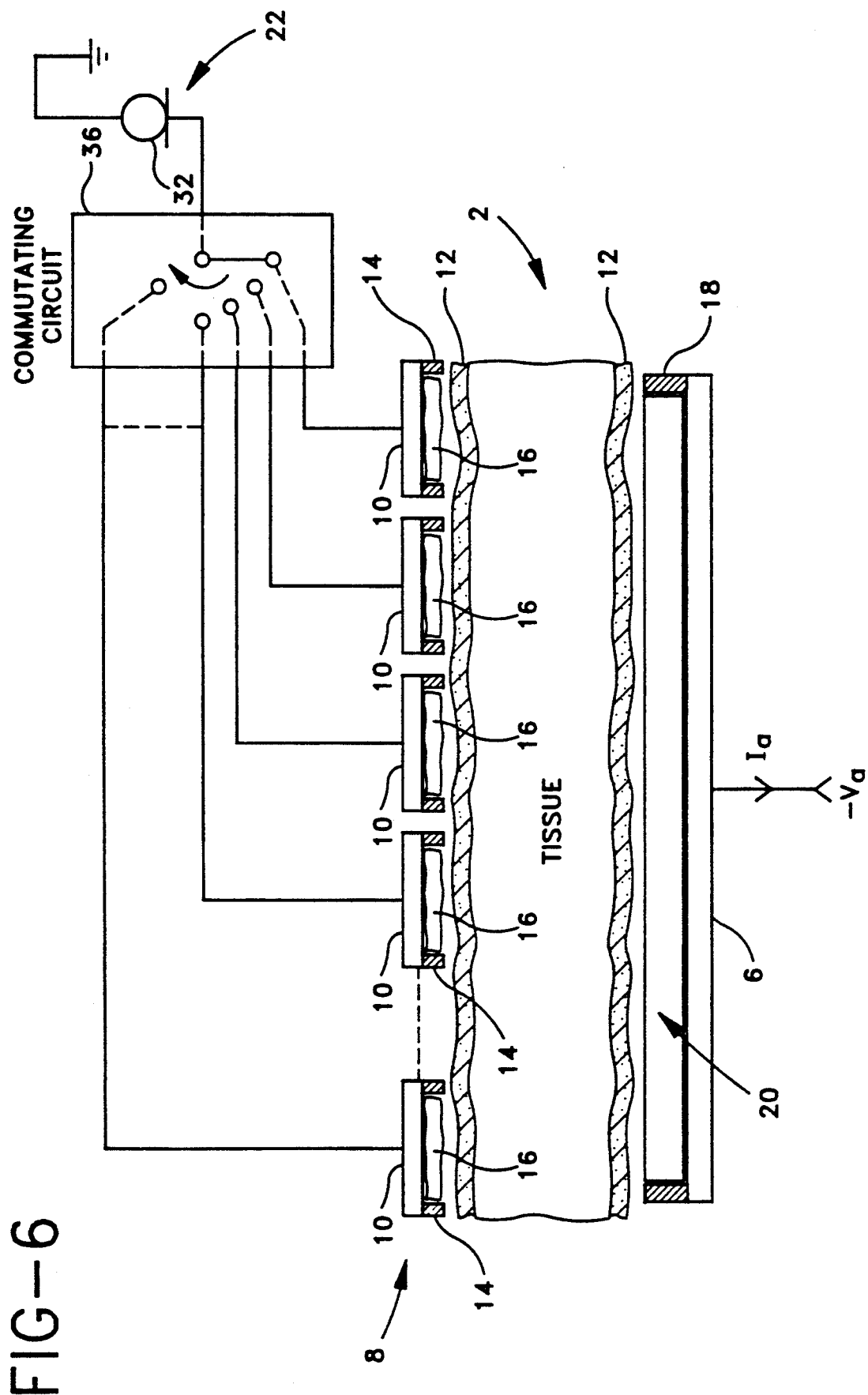
FIG. 6 is a cross-sectional view of a sixth alternative embodiment of a drug delivery device and circuit therefor, formed in accordance with the present invention.

FIG. 6 illustrates an alternative embodiment for the circuit of the present invention which controls and equalizes the current passing through each of the electrode segments of the drug delivery device. Shown in FIG. 6 is a drug delivery device 2 with its anode electrode 8 divided into a plurality of electrode segments 10, as in the embodiments shown in FIGS. 3 and 4, although the same principles of the invention are applicable to a drug delivery device having a segmented cathode electrode 6, as shown in FIGS. 1 and 2.

In the embodiment shown in FIG. 6, a single constant current source 22, such as a current diode 32, is coupled to the input of a commutating or multiplexer circuit 36 (shown, for example, as a rotary switching circuit), whose multiple outputs are each coupled to a corresponding electrode segment 10 of the anode electrode 8. The commutating circuit 36 time multiplexes the delivery of current from the constant current source sequentially to each of the electrode segments 10 so that each segment receives substantially the same amount of current for substantially the same amount of time. Each pulse of current provided to any one electrode segment will be equal in duration but offset in time to any other current pulse provided to any other electrode segment. For example, if the drug delivery device includes five electrode segments 10, then preferably the commutating circuit 36 will provide to each electrode segment a pulse of current having a 20% duty cycle, although a shorter but equal duty cycle pulse may be provided to each electrode segment, with the remainder of the commutating period being a dead time where no current is provided to any segment.

There may be instances where it is desirable to have constant and controlled currents in unequal amounts flowing through different electrode segments of the drug delivery device. For example, if the drug delivery device is formed with electrode segments which are unequal in size, different current diodes or other constant current sources may be used to deliver constant but unequal currents to the various electrode segments. Thus, in the embodiments shown in FIGS. 2 and 4, for example, each current diode 32 may be individually selected to provide a particular constant current to the electrode segment to which it is connected.

Figure 7:
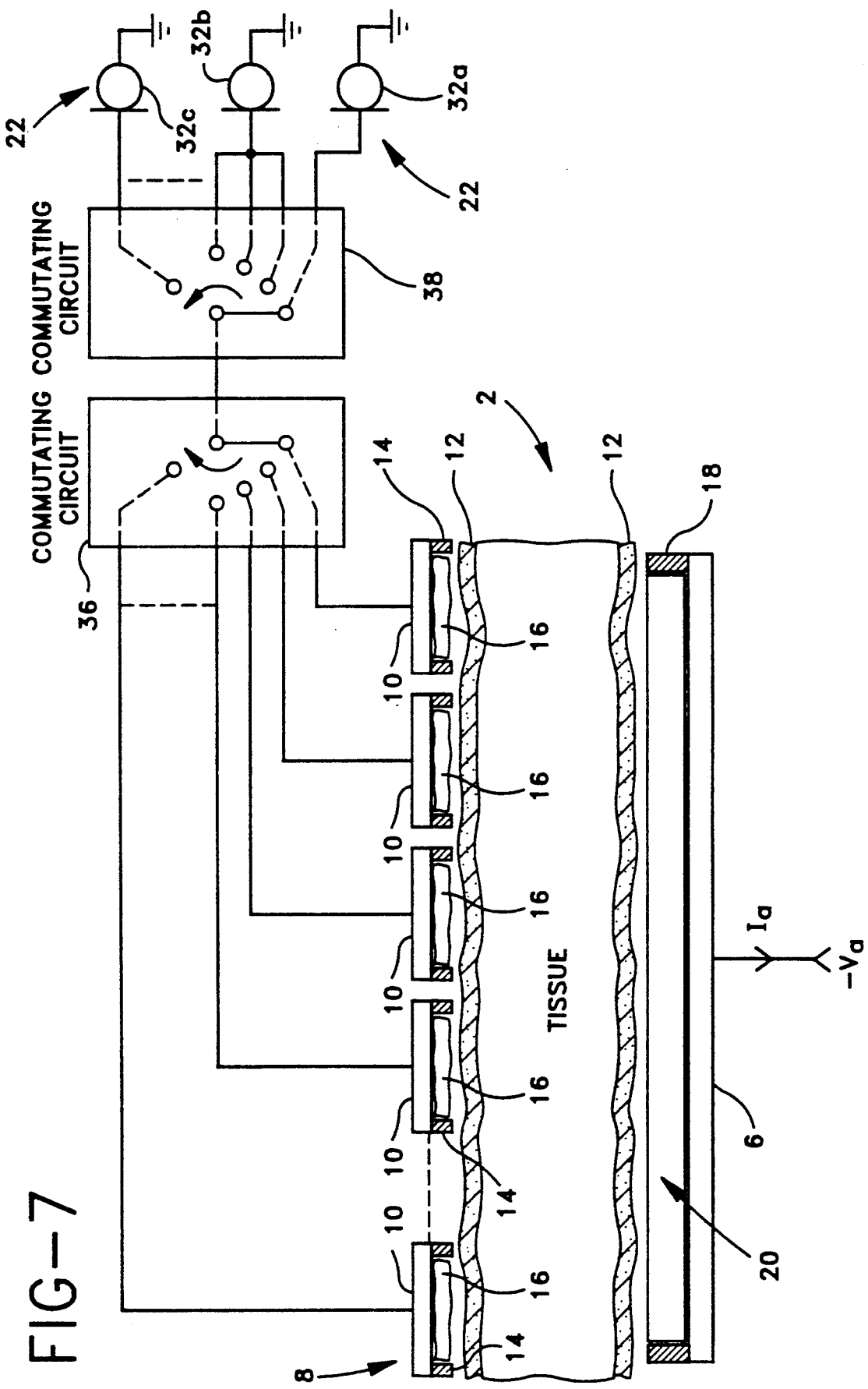
FIG. 7 is a cross-sectional view of a seventh embodiment of a drug delivery device and circuit therefor, formed in accordance with the present invention.

The same principle of having different, controlled currents applied in a time multiplex fashion is illustrated by FIG. 7. In the embodiment of FIG. 7, a commutating circuit 36, which may be a rotary switching circuit or other circuit, is coupled to the electrode segments 10 in the same manner as in the embodiment shown in FIG. 6. However, a second commutating circuit 38 is also used. The second commutating circuit 38 has a single output, which is coupled to the input of the first commutating circuit 36, and has multiple inputs. Each input is connected to a constant current source, such as current diodes 32a–32c. Each diode 32a–32c is chosen to supply a different desired amount of current to the segmented electrode. One or more inputs of the second commutating circuit 38 may be connected to the same current diode so that those associated electrode segments receive the same amount of current. The second commutating circuit 38 may be in the form of a rotary switching circuit or another circuit and coupled to the first commutating circuit 36 so that the two circuits switch concurrently. Thus, a desired amount of current will pass through the two commutating circuits 36, 38 from one of the current diodes 32a–32c at a time to each of the electrode segments 10 sequentially in a time multiplex fashion and in the same manner as described previously with respect to the embodiment shown in FIG. 6.

It should be realized that the same commutating circuits shown in FIGS. 6 and 7 may be used with a drug delivery device having a segmented cathode electrode, such as shown in FIG. 2, or with a drug delivery device having segmented anode and cathode electrodes, such as shown in FIG. 5, where the commutating circuits are connected between the electrode segments and one or more constant current sources.

The iontophoretic drug delivery device and current delivery circuit for the device ensure proper current levelling or equalization among the electrode segments, and avoid over-current conditions in skin pores or defects due to lower skin impedance situated adjacent to any one electrode segment. The constant current sources or other current controlling devices may be selected to provide the desired current flowing through each segment of the electrode and such that the current $I_a$ flowing through the iontophoretic device will be divided equally among each of the electrode segments. Accordingly, the iontophoretic device and current delivery circuit of the present invention will provide a substantially constant current density over the entire area of the electrodes and minimize any skin irritation or burning that may result due to changes in the impedance of the patient's skin.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An iontophoresis system, which comprises:
   an iontophoretic drug delivery device for placement against the skin of a patient, the drug delivery device including:
   a first electrode;
   means for holding an electrolyte situated in relation to the first electrode such that an electrolyte held by the electrolyte holding means is in electrical communication with the first electrode;
   a second electrode; and
   means for holding an ionic medication situated in relation to the second electrode such that an ionic medication held by the medication holding means is in electrical communication with the second electrode;
   at least one of the first and second electrodes being formed of a plurality of electrode segments; and
   means for controlling current passing through each of the electrode segments, the current controlling means including a plurality of constant current sources, each of the constant current sources of the plurality of sources being electrically coupled to a corresponding one of the electrode segments, the constant current sources being selected such that predetermined amounts of current flow through the electrode segments, wherein each constant current source is formed as a current mirror circuit, each current mirror circuit including a transistor electrically coupled to a corresponding electrode segment, and at least one reference diode, the transistor of each current mirror circuit being electrically coupled to the at least one reference diode, wherein current through the reference diode effectively controls the current flowing through each transistor.

2. An iontophoresis system as defined by claim 1, wherein the first electrode is a cathode and the second electrode is an anode, and wherein the first cathode electrode includes the plurality of electrode segments.

3. An iontophoresis system as defined by claim 1, wherein the first electrode is a cathode and the second electrode is an anode, and wherein the second anode electrode includes the plurality of electrode segments.

4. An iontophoresis system, which comprises:
   an iontophoretic drug delivery device for placement against the skin of a patient, the drug delivery device including:
   a first electrode;
   means for holding an electrolyte situated in relation to the first electrode such that an electrolyte held by the electrolyte holding means is in electrical communication with the first electrode;
   a second electrode; and
   means for holding an ionic medication situated in relation to the second electrode such that an ionic medication held by the medication holding means is in electrical communication with the second electrode;
   each of the first and second electrodes being formed of a plurality of electrode segments; and
   means for controlling current passing through each of the electrode segments, the current controlling means including a plurality of constant current sources, each of the constant current sources of the plurality of sources being electrically coupled to a corresponding electrode segment of at least one of the first electrode and the second electrode, the constant current sources being selected such that predetermined amounts of current flow through the electrode segments, wherein each constant current source is formed as a current mirror circuit, each current mirror circuit including a transistor electrically coupled to a corresponding electrode segment, and at least one reference diode, the transistor of each current mirror circuit being electrically coupled to the at least one reference diode, wherein current through the reference diode effectively controls the current flowing through each transistor.

5. An iontophoresis system, which comprises:
   an iontophoretic drug delivery device for placement against the skin of a patient, the drug delivery device including:
   a first electrode;
   means for holding an electrolyte situated in relation to the first electrode such that an electrolyte held by the electrolyte holding means is in electrical communication with the first electrode;
   a second electrode; and
   means for holding an ionic medication situated in relation to the second electrode such that an ionic medication held by the medication holding means is in electrical communication with the second electrode;
   at least one of the first and second electrodes being formed of a plurality of electrode segments; and
   means for controlling current passing through each of the electrode segments, the current controlling means including at least one constant current source and means for time multiplexing the flow of current through each of the electrode segments so that predetermined amounts of current flow through the electrode segments, during multiplexed time periods the current multiplexing means being in electrical communication with the constant current source and the electrode segments.

6. An iontophoresis system as defined by claim 5, wherein the current controlling means includes a first commutating circuit and a second commutating circuit, the first commutating circuit having an input and a plurality of outputs, each output of the first commutating circuit being coupled to a corresponding electrode segment, the second commutating circuit having an output and a plurality of inputs, the output of the second commutating circuit being coupled to the input of the first commutating circuit, at least one of the outputs of the second commutating circuit being coupled to the constant current source such that current from the constant current source passes through the first and second commutating circuits and at least one of the electrode segments.

7. An iontophoresis system as defined in claim 5, wherein the current controlling means includes a commutating circuit, the commutating circuit having an input and a plurality of outputs, each output of the commutating circuit being coupled to a corresponding electrode segment, the input of the commutating circuit being coupled to the at least one constant current source.

* * * * *